United States Patent
Beurle et al.

(10) Patent No.: US 10,492,754 B2
(45) Date of Patent: Dec. 3, 2019

(54) REAL-TIME CLOUD-BASED VIRTUAL FRACTIONAL FLOW RESERVE ESTIMATION

(71) Applicant: INTERNATIONAL BUSINESS MACHINES CORPORATION, Armonk, NY (US)

(72) Inventors: Darcy Beurle, West Melbourne (AU); Colin Compas, San Jose, CA (US); Stephen Moore, Melbourne (AU); Christine Schieber, Southbank (AU); Sergiy Zhuk, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1000 days.

(21) Appl. No.: 14/947,004

(22) Filed: Nov. 20, 2015

(65) Prior Publication Data

US 2017/0147778 A1 May 25, 2017

(51) Int. Cl.
*A61B 6/00* (2006.01)
*A61B 5/0275* (2006.01)
(Continued)

(52) U.S. Cl.
CPC .......... *A61B 6/563* (2013.01); *A61B 5/02007* (2013.01); *A61B 5/0275* (2013.01);
(Continued)

(58) Field of Classification Search
CPC ..... A61B 5/026; A61B 5/7267; A61B 5/7278; A61B 5/02007; A61B 5/021; A61B 6/032; A61B 6/507; A61B 6/5217; A61B 2034/105; A61B 2560/0475; A61B 2576/023; A61B 34/10; A61B 5/0022; A61B 5/0037; A61B 5/0044; A61B 5/02028; A61B 5/0205; A61B 5/024; A61B 5/0263; A61B 5/029; A61B 5/107; A61B 5/1073; A61B 5/14535; A61B 5/14546; A61B 5/7275; A61B 5/7282; A61B 5/742; A61B 5/743; A61B 6/463; A61B 6/503;
(Continued)

(56) References Cited

U.S. PATENT DOCUMENTS

9,087,147 B1   7/2015 Fonte
9,119,540 B2   9/2015 Sharma et al.
(Continued)

*Primary Examiner* — Aklilu K Woldemariam
(74) *Attorney, Agent, or Firm* — Tutunjian & Bitetto, P.C.; Grant Johnson (57) ABSTRACT

A system for estimating fractional flow reserve (FFR) includes a front end application to receive image frames from an imaging system to develop a model of a vasculature system based on an observed concentration time profile at locations within the model using contrast dye in the vasculature system and movement of the vasculature system. A graphics processing unit is configured to represent a computed concentration time profile in the vasculature system using a Lattice-Boltzmann Method (LBM) to generate a representation of the vasculature system. A dynamic controller tunes a velocity field based on a mismatch between the observed concentration time profile and the computed concentration time profile at the locations within the model to obtain a best estimate of the velocity field to perform a FFR measurement.

19 Claims, 5 Drawing Sheets

(51) Int. Cl.
*A61B 5/02* (2006.01)
*G16H 50/50* (2018.01)

(52) U.S. Cl.
CPC .............. *A61B 6/467* (2013.01); *A61B 6/504* (2013.01); *A61B 6/5211* (2013.01); *G16H 50/50* (2018.01); *A61B 6/481* (2013.01)

(58) Field of Classification Search
CPC .......... A61B 6/504; A61B 6/563; A61B 8/02; A61B 8/04; A61B 8/065; A61B 8/5223; A61B 5/02035; A61B 5/0285; A61B 5/7225; A61B 8/12; A61B 6/481; A61B 5/7246; A61B 5/7264; A61B 5/746; A61B 6/5211; A61B 8/0883; A61B 8/0891; A61B 8/06; A61B 5/1118; A61B 2576/00; A61B 8/463; G06F 19/00; G06F 17/10; G06F 17/11; G06F 17/5009; G06F 19/321; G06F 19/3468; G06F 19/3437; G06F 17/30; G06F 19/34; G06F 19/12; G06F 19/324; G16H 50/50; G16H 50/20; G16H 20/17; G16H 30/20; G16H 30/40; G16H 50/70; G16H 50/30; G16H 10/40; G16H 10/60; G06N 7/005; G06N 99/005; G06T 19/00; G06T 2207/10081; G06T 2207/10096; G06T 2207/10116; G06T 2207/30048; G06T 2207/30104; G06T 2210/41; G06T 7/0016; G06T 7/0014; G06T 2207/30101; G06T 7/0012; G06T 2207/10072; G06T 2207/30172; G06T 2200/04; G06T 17/00; G06T 2207/10132; G06T 7/00; G06T 2207/20072; G06T 7/55; G06T 11/008; G06T 2207/20044; G06T 2211/404; G06T 11/006; G06T 2211/421; G06T 7/70; Y02A 90/26; A61M 5/007; A61M 2210/12; G01R 33/5635; G06K 2009/4666; G06K 9/6215
USPC ........ 382/128, 131; 600/407, 431, 425, 504, 600/481, 508
See application file for complete search history.

(56) References Cited

U.S. PATENT DOCUMENTS

| | | | | |
|---|---|---|---|---|
| RE46,562 E * | 10/2017 | Huennekens | | |
| 2014/0037049 A1 * | 2/2014 | Langan | .................. | A61B 6/032 378/20 |
| 2014/0073976 A1 | 3/2014 | Fonte et al. | | |
| 2014/0088414 A1 * | 3/2014 | Mittal | .................... | A61B 6/481 600/425 |
| 2014/0142398 A1 * | 5/2014 | Patil | ........................ | A61B 6/463 600/301 |
| 2014/0200867 A1 * | 7/2014 | Lavi | ...................... | G06F 19/321 703/2 |
| 2014/0243662 A1 * | 8/2014 | Mittal | .................... | A61B 6/481 600/425 |
| 2014/0275947 A1 * | 9/2014 | Fonte | .................... | G06T 7/0012 600/407 |
| 2015/0302139 A1 * | 10/2015 | Sankaran | ............. | A61B 5/7275 703/20 |
| 2015/0339847 A1 * | 11/2015 | Benishti | ................. | G16H 50/30 382/131 |
| 2015/0342551 A1 * | 12/2015 | Lavi | ...................... | G16H 50/30 600/431 |
| 2016/0247279 A1 * | 8/2016 | Lavi | ...................... | G16H 50/50 |
| 2016/0342765 A1 * | 11/2016 | Sankaran | ............. | A61B 5/7275 |
| 2017/0032097 A1 * | 2/2017 | Itu | ............................ | G16H 50/50 |
| 2017/0147778 A1 * | 5/2017 | Beurle | ..................... | A61B 5/0275 |
| 2017/0296055 A1 * | 10/2017 | Gardner | ............... | G01N 21/359 |

* cited by examiner

REAL-TIME CLOUD-BASED VIRTUAL FRACTIONAL FLOW RESERVE ESTIMATION

BACKGROUND

Technical Field

The present invention relates to flow computation, and more particularly to systems and methods for estimating fractional flow reserve from angiograms.

Description of the Related Art

In the treatment of coronary artery disease, there are a number of tools available to a clinician, including a traditional x-ray angiogram, as well as more advanced fractional flow reserve (FFR) or optical coherence tomography (OCT) techniques. With an x-ray angiogram, a catheter is inserted into a major systemic artery and guided to the coronary vasculature where a radio-opaque dye is released that will mix with the flowing blood and reveal the vascular geometry. While this technique can provide anatomical information regarding stenosed lesions, the well-known 'FAME' trial indicated that patient outcomes were significantly improved when treatment was guided by a combination of both anatomical and functional information, as provided by FFR.

With this latter technique, a different catheter equipped with a pressure transducer is inserted and guided to a stenosed region of the coronary vasculature and transient pressure recordings are acquired both upstream and downstream of the lesion such that a measure of the pressure drop can be made. Despite the effectiveness of FFR, the increased cost of both a disposable catheter and clinician's time, plus the increased radiation exposure and potential damage to the arterial wall has meant that it is only utilized in a relatively small proportion of cases.

For this reason, there is a desire to quantify the pressure drop through a stenosis by other means. One promising technique is computational fluid dynamics. In this scenario, a computer model of the coronary vasculature can be created from an x-ray angiogram using either commercial or in-house software, then subsequently a three-dimensional (3D) computational mesh is created and the incompressible Navier-Stokes equations may be solved to obtain the velocity and pressure fields, known as virtual FFR or vFFR. Shortcomings of these techniques are in terms of the workflow and lead time necessary to produce a result and/or the specification of boundary conditions necessary to obtain a unique and patient-specific solution to the Navier-Stokes equations.

The workflow for extracting a geometrical model of a coronary vasculature, namely creating a 3D computational mesh, running a computational fluid dynamics (CFD) simulation, and post-processing the result, tends to be performed with a series of commercial engineering (or similar style) software packages, which would require input from a user skilled in this field and may be infeasible in a clinical setting.

Failing that, a medical image dataset may be uploaded through a web browser with the workflow performed elsewhere, but in either case the time required will be far greater than that for an FFR procedure. In terms of obtaining a unique and patient-specific model of the hemodynamic flow field in the coronary arteries, the options are either to specify pressures at the inlet and outlet/s of the model, or specify velocities (or equivalently flow rates) at the inlet and some form of 'outflow' condition at the outlets.

In practice, none of this information is readily available since flow rates are not measured as part of a standard angiographic procedure and while pressures could be recorded, this would require performing an FFR procedure, which would circumvent the need for performing the CFD simulation in the first place. While it may be tempting to try and use 'standard' values for flow rates or pressures in the larger arterial branches, this is problematic given the very patient-specific form of a stenosis, combined with the fact that vasodilatory drugs are given to increase the flow rate and hence pressure drop through the artery while pressure measurements are made.

In recent years, there have been significant efforts in the application of CFD to compute FFR. A vFFR measurement approach may be based on using computed tomography (CT) data to generate the geometry, which is acquired in a different clinical setting to where an x-ray angiogram is employed. As such, the turnaround time is much longer than would be acceptable in an interventional cardiology procedure. Furthermore, this service does not address the issue of patient-specific boundary conditions to the Navier-Stokes equations, which are needed in obtaining accurate results.

SUMMARY

A system for estimating fractional flow reserve (FFR) includes a front end application to receive image frames from an imaging system to develop a model of a vasculature system based on an observed concentration time profile at locations within the model using contrast dye in the vasculature system and movement of the vasculature system. A graphics processing unit is configured to represent a computed concentration time profile in the vasculature system using a Lattice-Boltzmann Method (LBM) to generate a representation of the vasculature system. A dynamic controller tunes a velocity field based on a mismatch between the observed concentration time profile and the computed concentration time profile at the locations within the model to obtain a best estimate of the velocity field to perform a FFR measurement.

A method for estimating fractional flow reserve (FFR) includes receiving image frames from an imaging system to develop a model of a vasculature system based on an observed concentration time profile at locations within the model using contrast dye in the vasculature system and movement of the vasculature system; representing a computed concentration time profile in the vasculature system using a Lattice-Boltzmann Method (LBM) to generate a representation of the vasculature system; and tuning a velocity field based on a mismatch between the observed concentration time profile and the computed concentration time profile at the locations within the model to obtain a best estimate of the velocity field to perform a FFR measurement.

A non-transitory computer readable storage medium includes a computer readable program for estimating fractional flow reserve (FFR), wherein the computer readable program when executed on a computer causes the computer to perform steps of receiving image frames from an imaging system to develop a model of a vasculature system based on an observed concentration time profile at locations within the model using contrast dye in the vasculature system and movement of the vasculature system; representing a computed concentration time profile in the vasculature system using a Lattice-Boltzmann Method (LBM) to generate a representation of the vasculature system; and tuning a velocity field based on a mismatch between the observed concentration time profile and the computed concentration time profile at the locations within the model to obtain a best estimate of the velocity field to perform a FFR measurement.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

In accordance with the present principles, systems and methods are provided to produce virtual fractional flow reserve (vFFR) data from an x-ray angiogram alone, in real-time, removing the complex workflow and uncertainty in a specification of boundary conditions. An automated and fast computational fluid dynamics (CFD) solver is employed in combination with a dynamic controller. Although computational power is continually increasing, the ability to perform detailed three-dimensional (3D) solutions to the Navier-Stokes equations in real-time using continuum mechanics models with unstructured computational grids is still infeasible. This is compounded by the fact that despite the increasing sophistication of commercial or open source software, completely automated mesh generation configuration and execution of a CFD simulation is also still infeasible.

To circumvent this problem, the present principles use a Lattice-Boltzmann Method (LBM) on an accelerator such as a Graphics Processing Unit (GPU). Similar to the Navier-Stokes equations, a Lattice-Boltzmann Method is a continuum model, described by a governing partial differential equation (the Boltzmann equation), but unlike the Navier-Stokes equations, it is derived from a fundamentally different approach. The particular type of discretization result in an algorithm that is simple, fast, and very scalable. Furthermore, grid generation can easily handle complex geometries. The image processing applied to the angiographic images can produce a 3D skeleton of the coronary vasculature, which is defined by a collection of coordinate points in 3D space, and line segments connecting these points. At each point a measure of the arterial diameter/radius is also taken from the angiograms. Using the skeletal curve and radius data, a 3D surface geometry can be created, and by overlaying this surface on a 3D voxel based structure, voxels/lattice points can be assigned to be either fluid, not-fluid, or inlet/outlet/wall type boundary points. An advantage of this approach is that the simulation time would be orders of magnitude faster than a full 3D solution to the Navier-Stokes equations, and the mesh generation procedure can be completely automated and performed in an insignificant amount of time (of the order of a second or less).

In accordance with useful embodiments, a dynamic controller is provided to tune the velocity field. While neither flow rates nor pressures are measured during an angiographic procedure to be used as boundary conditions in conventional approaches for simulating blood flow, there is some flow field information by virtue of the fact that motion of a radio-opaque dye can be observed as it flows through a vasculature. Known as TIMI (Thrombolysis in Myocardial Infarction) frame count, this approach of manually observing the time needed for the dye to traverse an artery (of quantifiable length) can be employed to infer boundary condition information.

In another embodiment, an additional transport equation may be solved along with the Navier-Stokes equations to generate a computed motion of the dye through the vasculature. It is then possible to define a cost function between the simulated and observed motion of the dye and solve an optimization problem where the boundary conditions could be dynamically adjusted to minimize this cost function. It may be inferred that the correct patient specific boundary conditions may be imposed and that the resulting pressure and velocity field are representative of the in-vivo analogue, and then the FFR result can be presented to a clinician. The need for iterative adjustment of the boundary conditions and re-computation of the flow field exacerbates the need for a fast CFD solver to be able to produce results in real-time, but also means that this aspect of the workflow, namely the configuration of a simulation and specification of boundary conditions, can be completely automated.

In one implementation of a tool in accordance with the present principles, a fast GPU based LBM fluid 'forward' solver employs the dynamic controller and image processing software to compute and dynamically track vascular centerlines for the purposes of defining a grid and extracting an observed motion of the dye, and the development of web based front end and cloud-based back end.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will also be understood that when an element is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C).

This may be extended, as readily apparent by one of ordinary skill in this and related arts, for as many items listed.

Figure 1:
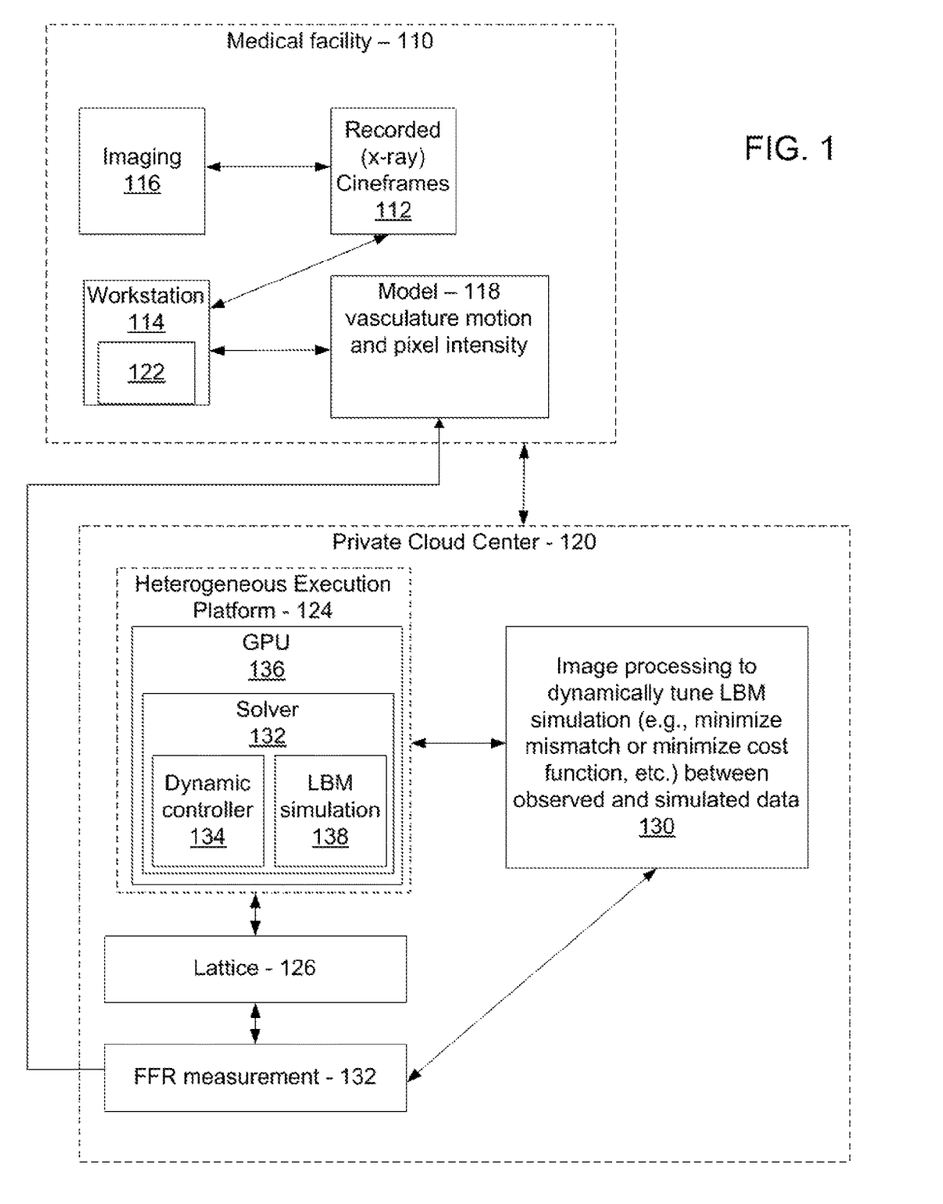
FIG. 1 is a block/flow diagram showing a system/method for estimating fractional flow reserve (FFR) in a cloud environment in accordance with the present principles.

Referring now to the drawings in which like numerals represent the same or similar elements and initially to FIG. 1, a schematic illustration of a system 100 for computing vFFR in real-time is illustratively shown in accordance with the present principles. In one embodiment, a catheter laboratory 110 or other clinical environment including hospital suites, medical facilities, etc. generates a time series of angiographic images or files 112, which are recorded and stored on a radiographer workstation 114. This may be performed in real-time during a procedure with a patient present or may be performed by recording the images and performing the analysis at a later time.

The angiographic images 112 may include cineframes from an imaging system 116, such as an x-ray machine, although other imaging techniques may be employed. In particular, the imaging system 116 collects images 112 of a particular vasculature. The vasculature is mapped out digitally to create a skeletal model 118.

In one example, the skeletal model 118 includes a model of arterial centerlines (skeleton), which can be visualized as a set of line segments, defined by a set of coordinate points in 3D space. At each point a measure of the diameter of the artery is made. Software creates these skeletons from angiographic images on a front end 122.

The imaging system 116 can track flow in the vasculature using contrast dyes known in the art. The dyes are injected into a patient to render at least some flow images, which can be visually tracked in the angiographic images 112.

A radiographer workstation 114 interacts with the front end 122 (e.g., web-based) of a service. The service may be located locally in the lab 110, as well. The front end 122 opens files 112, which may include Digital Imaging and Communications in Medicine (DICOM) or other image format files and creates the model 118 of a coronary vasculature that includes deformation of the vessels and intensity images at these deforming points along the skeleton, over a cardiac cycle. The intensity changes within the images 112 indicate flow patterns and deformation points within the vasculature. The model 118 and observations may be transferred to a cloud-based service 120, although the service may be local. The vessel skeleton model 118 is employed as input and employed to create a voxelization of a lattice into fluid and solid nodes based on the skeleton model 118 (centerlines of blood vessels). This process may be completely automated or performed by clinicians.

A surface model is created based on the skeleton model 118, and then the surface model is overlaid on a 3D voxel based data structure. The voxels can be assigned to be either inside the surface, outside the surface, or on the inlet/outlet/wall boundary with some form of numerical code. This is a 'lattice' 126 for a lattice Boltzmann simulation and can be done completely automatically in a run time of the order of a second or so.

The cloud-based service 120 creates the lattice 126 and defines all the lattice nodes appropriately. This may include identification of fluid, inlets, outlets, empty nodes, vessel walls, etc. in the nodes of the lattice 126. A controlled LBM simulation 138 is performed by a heterogeneous execution platform 124 of the cloud service 120. The LBM simulation 138 and dynamic controller 134 are part of a solver 132 that dynamically tunes the boundary conditions (or velocity field) with an image processor 130 until any mismatch between the observed and simulated data is understood.

The heterogeneous execution platform 124 may include an automated and fast computational fluid dynamics (CFD) solver 132 employed in combination with a dynamic controller 134. The solver 132 with the LBM simulation 138 and dynamic controller 134 are run on an accelerator such as a Graphics Processing Unit (GPU) 136. The GPU based LBM fluid 'forward' solver 132 employs the dynamic controller 134 and image processing software 130 to compute and dynamically track vascular centerlines for the purposes of defining the grid/lattice 126 and extracting an observed motion of the dye.

Similar to the Navier-Stokes equations, the LBM is a continuum model, described by a governing partial differential equation (the Boltzmann equation) and is orders of magnitude faster than a full 3D solution to the Navier-Stokes equations. The discretization result using the LBM simulation 138 is simple, fast, and very scalable. The LBM simulation 138 generates a grid or lattice 126 that can easily handle complex geometries. Grid and lattice geometry generation is known in the art. The simulation time and the mesh generation procedure are reduced to simply taking the vessel model 118, as input and creating a voxelization of a lattice 126 into fluid and solid nodes based on centerlines, which could be completely automated or performed by clinicians or a combination thereof. For example, a grid of voxels (3D pixels) is generated where each voxel represents a region of the model 118.

The dynamic controller 134 is provided to infer boundary conditions. Flow field information is obtained from the images 112 by virtue of the fact that motion of a radio-opaque dye can be observed as it flows through the vasculature. TIMI frame count is employed to observe the time needed for the dye to traverse a vessel (e.g., an artery of quantifiable length) and can be employed to infer boundary condition information. The TIMI frame count is a quantitative method for assessing coronary artery flow. The TIMI frame count is a simple continuous angiographic index, which counts the number of cineframes needed for contrast material to reach standard distal coronary landmarks.

The dynamic controller 134 may include a centralized processor or software program that possesses a global view of the vasculature (model 118). The vasculature may be considered a network with different branch flows. Whenever a node in the vasculature receives or discovers a new flow, it requests the controller 134 to install appropriate forwarding rules along the desired flow path (boundary conditions). The dynamic controller 134 maintains a consistent view of the vasculature network. As network flow patterns and volumes at different locations vary over time, the dynamic controller 134 reacts to dynamically re-adjust the network model to achieve the policy constraints (define or adjust the boundary conditions). The boundary conditions may include pressures, flow rate, flow volume or other characteristics of blood flow in the vasculature structure.

Also, in terms of the dynamic controller 134, there are a number of ways in which to tune the simulation. If concentration time profiles are recorded at various points on the curves of the skeletal model 118 then the controller 134 can either use a mismatch between the observed and computed concentration profiles, to update the boundary conditions, or to update the velocity field directly. While updating the boundary conditions is simpler, it needs to have the flow field be iteratively recomputed a number of times, with an updated boundary condition each time. The direct velocity field computation approach only needs one simulation, but will employ a more complex control algorithm. In the latter case, the simulation is dynamically tuned (block 130) by directly updating the solution, not just the boundary conditions.

In another embodiment, an additional transport equation may be solved along with the Navier-Stokes equations to generate a computed motion of the dye through the vasculature. A cost function between the simulated and observed motion of the dye may be computed to solve an optimization problem where the boundary conditions could be dynamically adjusted to minimize this cost function. The cost function may be employed with the dynamic controller approach or with the transport equation comparison approach. In either case, the correct patient specific boundary conditions may be inferred and imposed. The resulting pressure and velocity fields are representative of the in-vivo analogue and then the vFFR result may be obtained. The process may be iterative to adjust the boundary conditions and re-compute the flow field. The fast CFD solver 132 is able to produce results in real-time, but also means that this aspect of the workflow, namely the configuration of a simulation and/or specification of boundary conditions can be completely automated.

In accordance with the present principles, the vFFR can be computed from x-ray angiogram images 112 alone in real-time. This removes the complex workflow and uncertainty associated with specification of boundary conditions in conventional techniques. The vFFR measurement using the tuned boundary conditions (or the direct velocity flow) is provided in block 134 and sent back to the web front end 122 for use by a practitioner is real-time.

While FIG. 1 provides a network configuration for providing vFFR services, the present principles may be performed on a single computer device or distributed over multiple computer devices. In addition, while vFFR is described for useful embodiments, other analyses may be performed using the angiogram image, LBM simulation and dynamic controllers.

Figure 2:
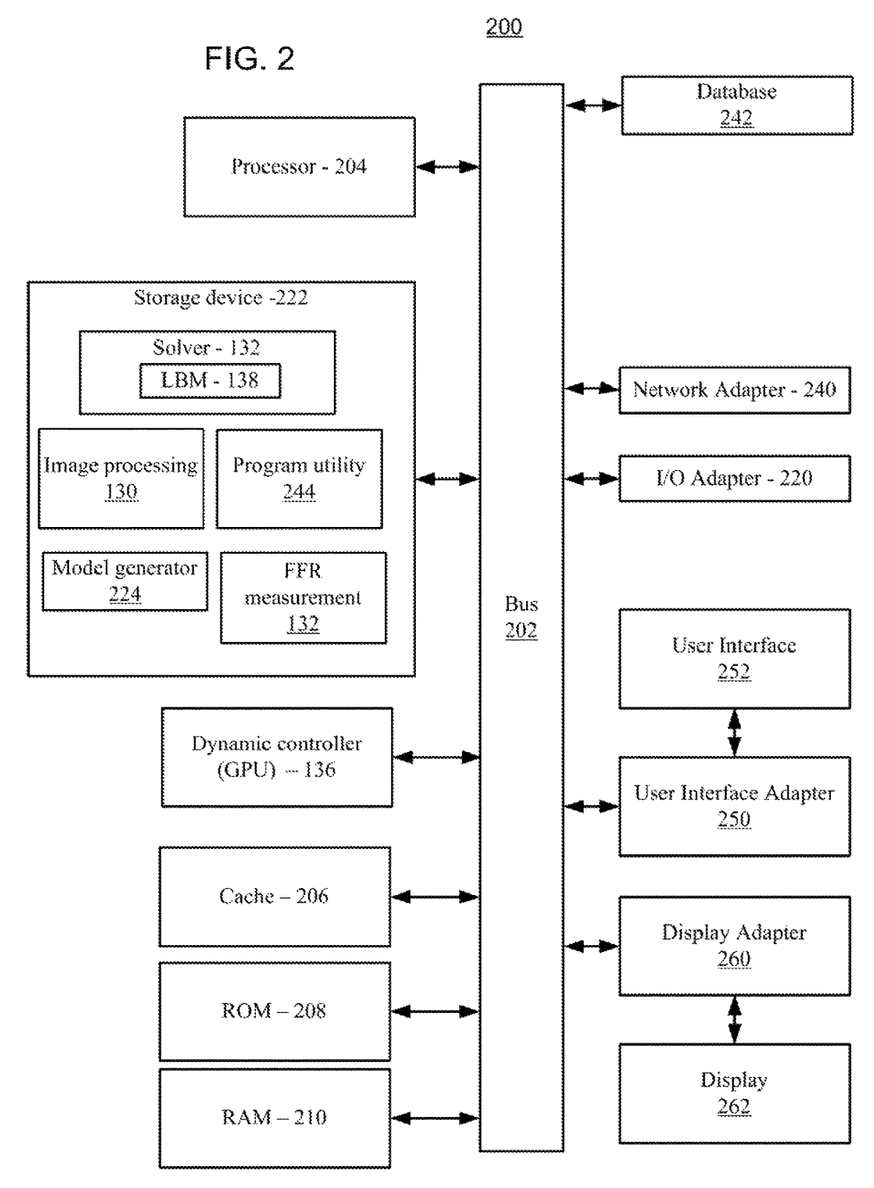
FIG. 2 is a block/flow diagram showing a system/method for estimating FFR in a local computer environment in accordance with the present principles.

Referring to FIG. 2, a block/flow diagram shows an exemplary processing system 200 for vFFR. The processing system 200 includes at least one processor (CPU) 204 operatively coupled to other components via a system bus 202. A cache 206, a Read Only Memory (ROM) 208, a Random Access Memory (RAM) 210, an input/output (I/O) adapter 220, a network adapter 240, a user interface adapter 250, and a display adapter 260 are operatively coupled to the system bus 202.

A user input device 252 may be operatively coupled to system bus 202 by the user interface adapter 250. The user input device(s) 252 can be any of a keyboard, a mouse, a keypad, an image capture device, a motion sensing device, a microphone, a device incorporating the functionality of at least two of the preceding devices, and so forth. Other types of input devices can also be employed, e.g., a touch screen display. The user input device 252 is employed to input and output information to and from system 200. A display 262 is coupled to the display adapter 260.

A first storage device 222 is operatively coupled to system bus 202 (and may be coupled directly or through the I/O adapter 220). The storage device 222 can be any of a disk storage device (e.g., a magnetic or optical disk storage device), a solid state magnetic device, etc. The first storage device 222 stores one or more programs that will be run on the system 200. The programs may include LBM simulation 138, image processing 130, solver 132, model generator 224 for generating the model 118 (e.g., the front end 122), and FFR measurement 132.

The system 200 may be included locally or may access wide area or global networks through the network adapter 240. The system 200 may include a database 242 for storing and updating lattices, boundary conditions, vasculature changes, etc. Graphics processing unit or units 136 may be employed as the dynamic controller 134, which work in conjunction with the LBM simulation program 138 and the image processing program 130.

The system for estimating FFR includes a front end application to receive image frames from an imaging system to develop a model of a vasculature system based on observed flow using contrast dye in the vasculature system and movement of the vasculature system. Furthermore, the system can record the time profile of concentration at a number of key positions within the model of the vascular system. A graphics processing unit is configured to represent a simulated flow in the vasculature system using a Lattice-Boltzmann Method (LBM) to generate a representation of the vasculature system. This simulated flow includes the spatially and temporally varying velocity field and concentration field, where the input time concentration profile matches that which the clinician used when acquiring the angiographic images. A dynamic controller tunes the simulated velocity field based on the mismatch between the observed and computed concentration time profiles at the key locations within the model of the vascular system, in order to obtain the best estimate of the velocity field, upon which point the pressure field and hence FFR measurement can be made.

The system 200 may include other elements (not shown), as readily contemplated by one of skill in the art, as well as omit certain elements. For example, various other input devices and/or output devices can be included in processing system 200, depending upon the particular implementation of the same, as readily understood by one of ordinary skill in the art. For example, various types of wireless and/or wired input and/or output devices can be employed. Moreover, additional processors, controllers, memories, and so forth, in various configurations can also be utilized as readily appreciated by one of ordinary skill in the art. These and other variations of the processing system 200 are readily contemplated by one of ordinary skill in the art given the teachings of the present principles provided herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows: On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: The provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows: Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): The capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): The capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows: Private cloud: the cloud infrastructure is operated solely for an organization. It may be managed by the organization or a third party and may exist on-premises or off-premises.

Community cloud: The cloud infrastructure is shared by several organizations and supports a specific community that has shared concerns (e.g., mission, security requirements, policy, and compliance considerations). It may be managed by the organizations or a third party and may exist on-premises or off-premises.

Public cloud: The cloud infrastructure is made available to the general public or a large industry group and is owned by an organization selling cloud services.

Hybrid cloud: The cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring again to FIG. 1, an example of a cloud computing node 120 is shown. Cloud computing node 120 is only one example of a suitable cloud computing node and is not intended to suggest any limitation as to the scope of use or functionality of embodiments of the invention described herein. Regardless, cloud computing node 120 is capable of being implemented and/or performing any of the functionality set forth hereinabove.

Referring again to FIG. 2 with continued reference to FIG. 1, a computer system/server 200, which is operational with numerous other general purpose or special purpose computing system environments or configurations may be configured as or with the cloud node 120. Examples of well-known computing systems, environments, and/or configurations that may be suitable for use with computer system/server 200 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 200 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 200 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system/server 200 (in cloud computing node 120, FIG. 1) is shown in the form of a general-purpose computing device. The components of computer system/server 200 may include, but are not limited to, one or more processors or processing units 204, a system memory 222, and a bus 202 that couples various system components including system memory 222 to processor 204.

Bus 202 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 200 includes a variety of computer system readable media. Such media may be any available media that is accessible by computer system/server 200, and it includes both volatile and non-volatile media, removable and non-removable media.

System 200 can include computer system readable media in the form of volatile memory, such as RAM 210, ROM 208 and/or cache memory 206. Computer system/server 200 may further include other removable/non-removable, volatile/non-volatile computer system storage media. By way of example only, storage device 222 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 202 by one or more data media interfaces. As will be further depicted and described below, memory 222 may include at least one program product having a set (e.g., at least one) of program modules that are configured to carry out the functions of embodiments of the invention.

A program/utility, having a set (at least one) of program modules, may be stored in memory 222 by way of example, and not limitation, as well as an operating system, one or more application programs, other program modules, and program data. Each of the operating system, one or more application programs, other program modules, and program data or some combination thereof, may include an implementation of a networking environment. Program modules (e.g., 130, 132, 138, 224, etc.) generally carry out the functions and/or methodologies of embodiments of the invention as described herein.

Computer system/server 200 may also communicate with one or more external devices such as a keyboard, a pointing device (252), a display 262, etc.; one or more devices that enable a user to interact with computer system/server 200; and/or any devices (e.g., network card, modem, etc.) that enable computer system/server 200 to communicate with one or more other computing devices. Such communication can occur via I/O interfaces 220. Still yet, computer system/server 200 can communicate with one or more networks such as a local area network (LAN), a general wide area network (WAN), and/or a public network (e.g., the Internet) via network adapter 240. Network adapter 240 communicates with the other components of computer system/server 200 via bus 202. It should be understood that although not shown, other hardware and/or software components could be used in conjunction with computer system/server 200. Examples, include, but are not limited to: microcode, device drivers, redundant processing units, external disk drive arrays, RAID systems, tape drives, and data archival storage systems, etc.

Figure 3:
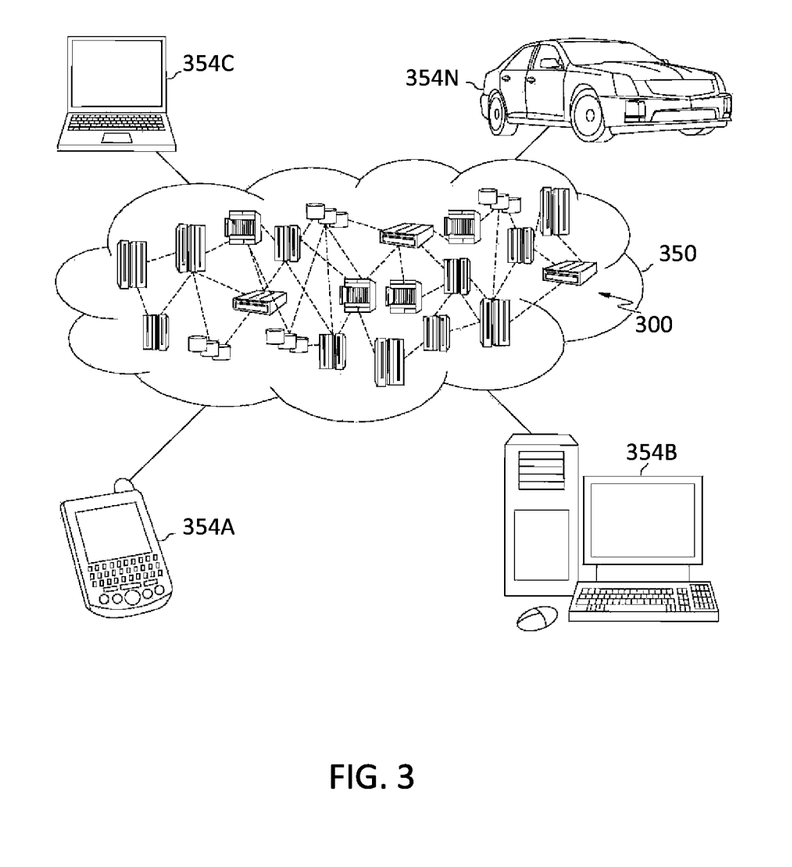
FIG. 3 is a block/flow diagram showing a cloud computing environment according to one embodiment.

Referring now to FIG. 3, an illustrative cloud computing environment 350 is depicted. As shown, cloud computing environment 350 comprises one or more cloud computing nodes 300 with which local computing devices used by cloud consumers, such as, for example, personal digital assistant (PDA) or cellular telephone 354A, desktop computer 354B, laptop computer 354C, and/or automobile computer system 354N may communicate. Nodes 300 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services (including FFR services or other medical computation services) for which a cloud consumer does not need to maintain resources on a local computing device. It is understood that the types of computing devices 354A-N shown in FIG. 3 are intended to be illustrative only and that computing nodes 300 and cloud computing environment 350 can communicate with any type of computerized device over any type of network and/or network addressable connection (e.g., using a web browser).

Figure 4:
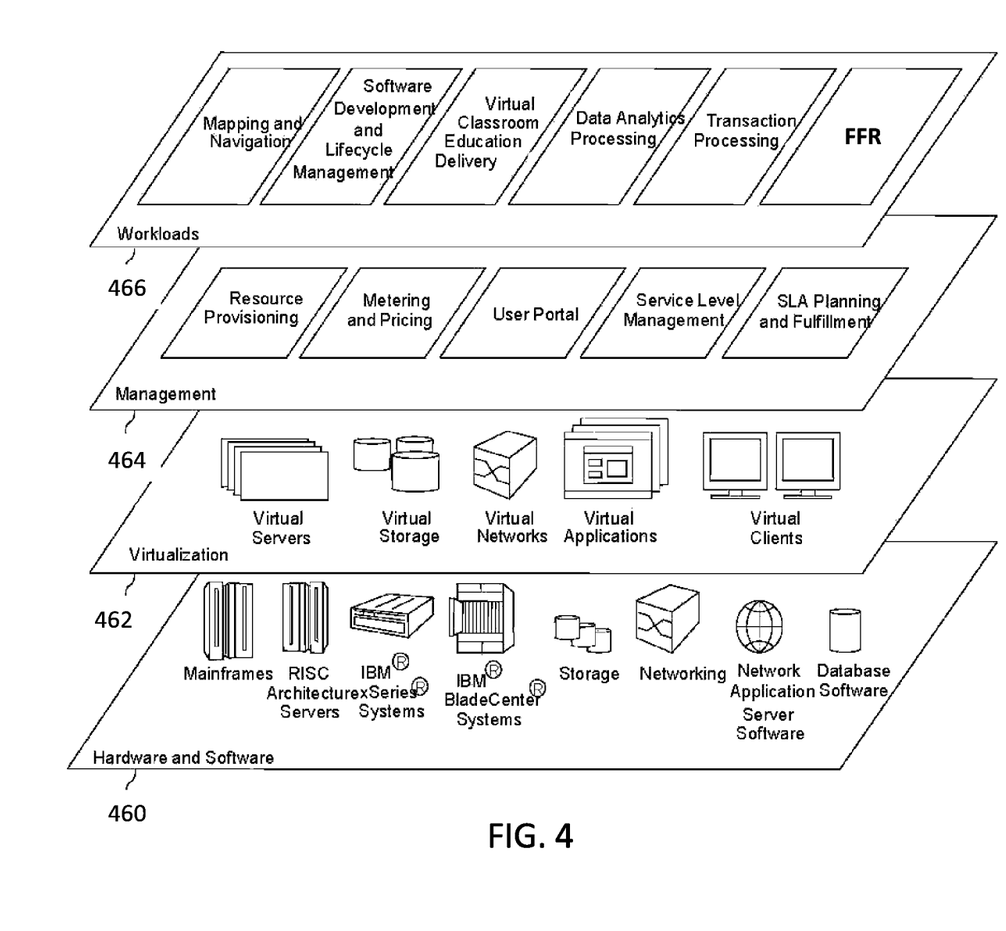
FIG. 4 is a block/flow diagram showing abstraction model layers according to one embodiment.

Referring to FIG. 4, a set of functional abstraction layers provided by cloud computing environment 350 (FIG. 3) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 460 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 462 provides an abstraction layer from which the following examples of virtual entities may be provided: virtual servers; virtual storage; virtual networks, including virtual private networks; virtual applications and operating systems; and virtual clients.

In one example, management layer 464 may provide the functions described herein. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer 466 provides examples of functionality for which the cloud computing environment may be utilized. Examples of workloads and functions which may be provided from this layer include: mapping and navigation; software development and lifecycle management; virtual classroom education delivery; data analytics processing; transaction processing; and FFR analytics to produce virtual fractional flow reserve (vFFR) data from an x-ray angiogram alone in real-time, removing the complex workflow and uncertainty in a specification of boundary conditions.

Figure 5:
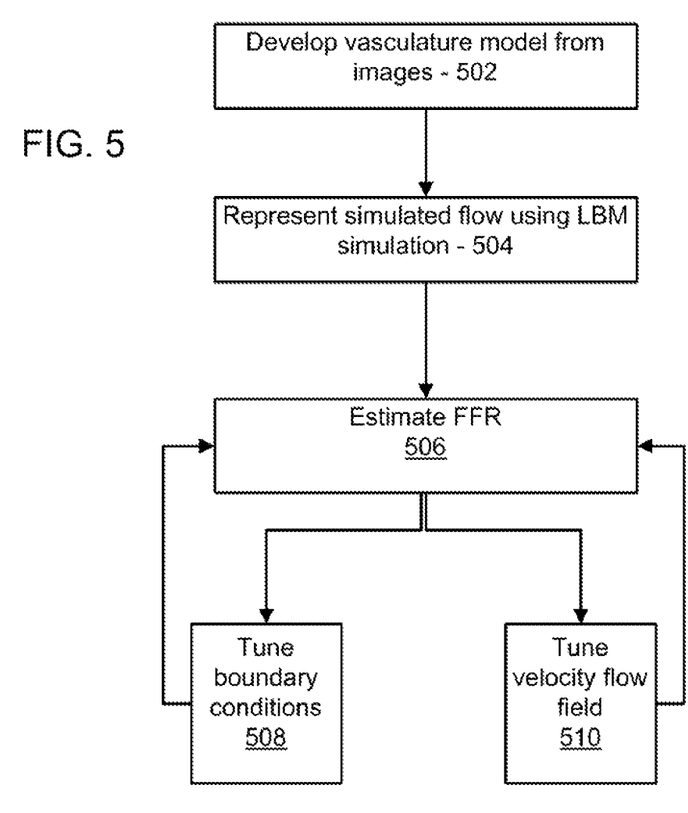
FIG. 5 is a block/flow diagram for a method for estimating FFR in accordance with illustrative embodiments.

Referring to FIG. 5, a method for estimating FFR is shown in accordance with the present principles. In block 502, image frames from an imaging system are received to develop a model (skeleton) of a vasculature system based on an observed concentration time profile at locations within the model using contrast dye in the vasculature system and movement of the vasculature system. The model may be developed using the medical images in real-time. The image frames may include angiographic images from an x-ray system. The observed flow may be measured using a thrombolysis in myocardial infarction (TIMI) frame count, which counts a number of cineframes needed for the contrast dye material to reach a landmark.

In block 504, a computed or simulated concentration time profile is generated for the vasculature system using a Lattice-Boltzmann Method (LBM) to generate a representation of the vasculature system at locations in the vasculature. The representation is preferably a nodal system or lattice with voxels representing static and moving portions in accordance with the images with contrast dye.

In block 506, a velocity field is tuned based on a mismatch between the observed concentration time profile and the computed concentration time profile at the locations within the model to obtain a best estimate of the velocity field to perform a FFR measurement. The FFR measurement includes similar information provided by Navier-Stokes fluid dynamics solutions. The FFR measurement may be provided as a service in a cloud environment. The FFR measurement is preferably provided in real-time.

In block 508, boundary conditions are dynamically tuned by the simulation with the LBM until no mismatch between observed and simulated data is achieved or other criteria are achieved. In one embodiment, the boundary conditions are dynamically adjusted to minimize a cost function. In block 510, a velocity flow field is dynamically tuned by the controller to use the mismatch between the observed and computed concentration profiles to update the velocity field directly.

The system can record the time profile of concentration at a number of key positions within the model of the vascular system. This simulated flow includes the spatially and temporally varying velocity field and concentration field, where the input time concentration profile matches that which the clinician used when acquiring the angiographic images. A dynamic controller tunes the simulated velocity field based on the mismatch between the observed and computed concentration time profiles at the key locations within the model of the vascular system, to obtain the best estimate of the velocity field, upon which point the pressure field and hence FFR measurement can be made.

Having described preferred embodiments for real-time cloud-based virtual fractional flow reserve estimation (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A system for estimating fractional flow reserve (FFR), comprising:
    a front end application to receive image frames from an imaging system to develop a model of a vasculature system based on an observed concentration time profile at locations within the model using contrast dye in the vasculature system and movement of the vasculature system, wherein the observed time profile of concentration is measured by counting a number of frames needed for the contrast dye material to reach a landmark;
    a graphics processing unit configured to represent a computed concentration time profile in the vasculature system using a Lattice-Boltzmann Method (LBM) to generate a representation of the vasculature system; and
    a dynamic controller to tune a velocity field based on a mismatch between the observed concentration time profile and the computed concentration time profile at the locations within the model to obtain a best estimate of the velocity field to perform a FFR measurement.

2. The system as recited in claim 1, wherein the image frames include angiographic images from an x-ray system.

3. The system as recited in claim 1, wherein the dynamic controller dynamically tunes boundary conditions of a simulation with the LBM until no mismatch between observed and simulated data is achieved.

4. The system as recited in claim 1, wherein the boundary conditions are dynamically adjusted to minimize a cost function.

5. The system as recited in claim 1, wherein the dynamic controller dynamically tunes a velocity flow field to use the mismatch between the observed and computed concentration profiles to update the velocity flow field directly.

6. The system as recited in claim 1, wherein the model of the vasculature is represented as a lattice with lattice nodes.

7. The system as recited in claim 1, wherein the observed time profile of concentration is measured using a thrombolysis in myocardial infarction (TIMI) frame count, which counts a number of cineframes needed for the contrast dye material to reach a landmark.

8. The system as recited in claim 1, wherein the simulated time profile of concentration includes a spatially and temporally varying velocity field and concentration field, where an input time concentration profile matches that which a clinician employed when acquiring the image frames.

9. The system as recited in claim 1, wherein the FFR measurement is provided as a service in a cloud environment.

10. A method for estimating fractional flow reserve (FFR), comprising:
    receiving image frames from an imaging system to develop a model of a vasculature system based on an observed concentration time profile at locations within the model using contrast dye in the vasculature system and movement of the vasculature system, wherein the observed time profile of concentration is measured using a thrombolysis in myocardial infarction (TIMI) frame count, which counts a number of cineframes needed for the contrast dye material to reach a landmark;
    representing a computed concentration time profile in the vasculature system using a Lattice-Boltzmann Method (LBM) to generate a representation of the vasculature system; and
    tuning a velocity field based on a mismatch between the observed concentration time profile and the computed concentration time profile at the locations within the model to obtain a best estimate of the velocity field to perform a FFR measurement.

11. The method as recited in claim 10, wherein the image frames include angiographic images from an x-ray system.

12. The method as recited in claim 10, wherein tuning includes dynamically tuning boundary conditions of a simulation with the LBM until no mismatch between observed and simulated data is achieved.

13. The method as recited in claim 12, wherein the boundary conditions are dynamically adjusted to minimize a cost function.

14. The method as recited in claim 10, wherein tuning includes dynamically tuning a velocity flow field to use the mismatch between the observed and computed concentration profiles to update the velocity flow field directly.

15. The method as recited in claim 10, wherein the simulated time profile of concentration includes a spatially and temporally varying velocity field and concentration field, where an input time concentration profile matches that which a clinician employed when acquiring the image frames.

16. The method as recited in claim 10, wherein the FFR measurement is provided as a real-time service in a cloud environment.

17. A non-transitory computer readable storage medium comprising a computer readable program for estimating fractional flow reserve (FFR), wherein the computer readable program when executed on a computer causes the computer to perform steps of:

receiving image frames from an imaging system to develop a model of a vasculature system based on an observed concentration time profile at locations within the model using contrast dye in the vasculature system and movement of the vasculature system, wherein the observed time profile of concentration is measured using a thrombolysis in myocardial infarction (TIMI) frame count, which counts a number of cineframes needed for the contrast dye material to reach a landmark;

representing a computed concentration time profile in the vasculature system using a Lattice-Boltzmann Method (LBM) to generate a representation of the vasculature system; and tuning a velocity field based on a mismatch between the observed concentration time profile and the computed concentration time profile at the locations within the model to obtain a best estimate of the velocity field to perform a FFR measurement.

18. The non-transitory computer readable storage medium as recited in claim 17, wherein tuning includes dynamically tuning boundary conditions of a simulation with the LBM until no mismatch between observed and simulated data is achieved.

19. The non-transitory computer readable storage medium as recited in claim 17, wherein tuning includes dynamically tuning a velocity flow field to use the mismatch between the observed and computed concentration profiles to update the velocity flow field directly.

\* \* \* \* \*